United States Patent [19]

Geho et al.

[11] Patent Number: 4,863,896
[45] Date of Patent: Sep. 5, 1989

[54] DIABETIC CONTROL BY COMBINED INSULIN FORMS

[75] Inventors: W. Blair Geho; John R. Lau, both of Wooster, Ohio

[73] Assignee: Technology Unlimited, Inc., Wooster, Ohio

[21] Appl. No.: 143,180

[22] Filed: Jan. 13, 1988

Related U.S. Application Data

[63] Continuation-in-part of Ser. No. 858,456, Apr. 30, 1986, abandoned, which is a continuation-in-part of Ser. No. 606,714, May 3, 1984, Pat. No. 4,603,044.

[51] Int. Cl.$^4$ ............................................. C07K 7/40
[52] U.S. Cl. .................................... 514/4; 514/3
[58] Field of Search ............................. 514/3, 4

[56] References Cited

U.S. PATENT DOCUMENTS 4,377,567  3/1983  Geho ........................... 424/1
4,603,044  7/1986  Geho et al. ..................... 514/3

Primary Examiner—Howard E. Schain
Assistant Examiner—F. T. Moezie
Attorney, Agent, or Firm—Frijouf, Rust & Pyle

[57] ABSTRACT

Peripherally administered insulin fails to provide liver hormone function. Hepatocyte directed vesicles with encapsulated insulin will restore liver function, but there is no non-targeted insulin to bypass the liver for peripheral use, as in natural, healthy body function.

Whenever a prescribed dosage of insulin is divided between free and encapsulated hepatocyte targeted forms, a very small fraction of the dose in encapsulated form is sufficient to elicit full liver function, and non-targeted insulin supplies the needs of the body muscle and tissue.

3 Claims, 6 Drawing Sheets

\* P <.05 compared to Regular Insulin treatment

\* P < .05 compared to Regular Insulin treatment

DIABETIC CONTROL BY COMBINED INSULIN FORMS

CROSS-REFERENCE TO RELATED APPLICATIONS

This application is a continuation-in-part of application Ser. No. 858,456, filed Apr. 30, 1986 now abandoned which is a continuation-in-part of application Ser. No. 606,714, filed May 3, 1984 now U.S. Pat. No. 4,603,044, issued July 29, 1986.

BACKGROUND OF THE INVENTION

1. Field of the Invention

This invention relates to an improved treatment of illness brought about by hormonal deficiency disease. More particularly, the invention is directed to the simultaneous but separate supply of substances deficient to the liver, and to peripheral body organs and tissue. Specifically, this invention is directed to the whole person treatment of diabetes Mellitus. A chemically structured targeted delivery system to the hepatocyte of the liver supplies the liver with insulin but not to the peripheral system. A separate and substantially simultaneous supply of regular free insulin which is not targeted to the liver supplies the peripheral body needs. The combination of the directed insulin and the free insulin enables a far lower dosage and better control.

2. Background Art

Diabetes Mellitus often occurs early in life by a severe reduction or complete absence of insulin production in the system. This deficiency results in abnormally high levels of glucose in the blood of afflicted patients and an inability of certain tissues to utilize glucose as a nutrient.

Diabetes mellitus is a disease in which the elevated levels of glucose and the inability of the body to metabolize glucose results in eventual death. The more complete the absence of insulin, the more rapid is the death.

The accepted therapy relied on prior to this invention is the subcutaneous administration of insulin. Such treatment while sustaining life, does not correct all biochemical abnormalities. Nor does it prevent the long term sequelae of the disease, which causes microvascular damage resulting in blindness, heart disease, strokes, kidney failure and death.

In this disclosure it is assumed that the patient has a healthy liver capable of proper uptake of glucose and subsequent dispensing of the glucose but for the absence of the regulating hormone insulin.

In the normal warm blooded animal body, intake of a meal triggers production of insulin which is taken up with the digested food and passed through the portal vein to the liver. The insulin is at least partially in control of the liver function in that when proper hormones are present, the liver will convert the glucose from digested food into glycogen and store that glycogen in the liver. Reconversion of glycogen to glucose takes place when blood level sugar is lowered.

It is known to be a fact, but not well understood, that in a normal healthy body, all of the insulin is not taken up by the liver at the time of insulin production. There is a certain quantity of the insulin that bypasses the liver into the peripheral system where it enables the muscle and fat tissue to take up the glucose and employ the glucose in energy production as well as body building.

The teaching of U.S. Pat. Nos. 4,377,567 and 4,603,044 is incorporated herein by reference. U.S. Pat. No. 4,377,567 and U.S. Pat. No. 4,603,044, both address the successful delivery of insulin to the liver by encapsulating the hormone in minute vesicles. The vesicles have target molecules that are recognized by the liver cells. The vesicles are thus taken into the liver for hormone liver function. Although quite successful in obtaining normal liver function, these inventions do not provide the exact mimic of nature in allowing some insulin to escape to the peripheral system. The liver of a healthy system accepts only part of the available insulin, whereas whenever insulin is delivered via the hepatocyte directed vesicles, the entire supply is taken into the liver and now is unavailable for the peripheral system.

SUMMARY OF THE INVENTION

This invention is embodied in the discovery that administering insulin in an hepatocyte directed vesicle together with a simultaneous supply of free insulin, results in a highly significant reduction in total daily dosage required to better control blood glucose within normal limits and to alleviate the complications of diabetes mellitus. Such complications involve three areas principally: carbohydrate metabolism, cardiovascular system and neurological system.

As used hereinafter, free insulin, or the abbreviation FI, will mean any form of insulin usable for alleviating the excess glucose in the circulatory system.

This invention utilizes newly emerging liposome technology that provides a novel treatment for diabetes mellitus therapy. It incorporates regular free insulin into a bipolar lipid vesicle that has on its surface certain molecules that direct the vesicle to the hepatocytes of the liver. This form of the insulin will be referred to as a hepatocyte directed vesicle with insulin or abbreviated HDVI. The HDVI will be taken up only by the liver. Separately administered free insulin in the conventional manner will supply the needs of the peripheral system. The extraordinary advantage discovered by this combination is the extreme reduction in the dosage of the free insulin required to substantially provide replication of healthy function.

According to this invention, a new and effective means to treat diabetes mellitus is accomplished by mixing a hepatocyte directed vesicle insulin (HDVI) which is targeted to the metabolic cells of the liver, with free insulin (FI) in a dose which is determined by the need of the host. The free insulin supplies the peripheral tissues, as is done with prior art injection therapy. However, the hepatocyte directed vesicle insulin bypasses the peripheral tissues and continues on to reach the hepatocytes of the liver, thus stimulating the liver to undertake the function of glucose uptake during meals. During non-meal time (fasting) the HDVI acts to control the rate of glucose production by the liver. Both the uptake of glucose by the liver during meals and the highly significant reduction of the rate of glucose release from the liver during fasting are not effectively treated by free insulin alone as done by the prior art.

The dangerous hypoglycemic side effect of free insulin alone as heretofore practiced, is far more effectively avoided. The test procedures and results are set forth hereinafter. Thus, the combination of HDVI-FI is both more efficient and safer than FI alone.

The primary object of this invention is to replicate as close as possible normal physiological functioning of the liver and circulatory system in utilizing glucose in a person who suffers with diabetes mellitus.

It is another object of the invention to enable a reduction in the dose of free insulin that the patient would otherwise be required to use while maintaining a fasting blood glucose level within the generally accepted normal range of blood glucose.

It is still a further object of the invention to effectively avoid the dangerous possibility of a hypoglycemic side effect sometimes caused by the use of free insulin alone. The consistency of response to a host employing the methods of this invention is responsible, as hereinafter more fully explained, for essentially completely avoiding insulin shock as often experienced by those employing larger peripheral subcutaneous injections of free insulin.

DETAILED DESCRIPTION OF THE INVENTION

Figure 1:
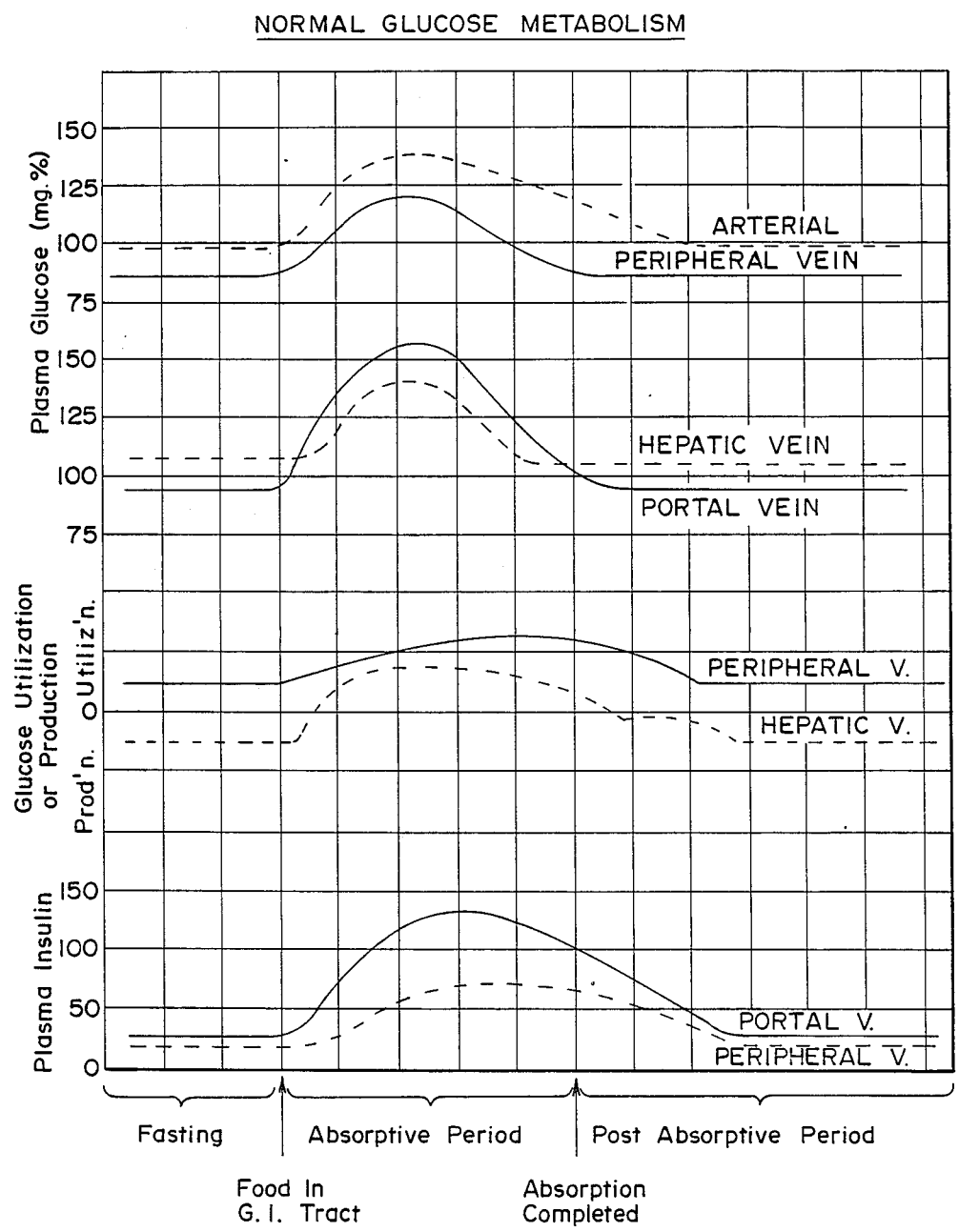
FIG. 1 is a multiple test graph showing in the first two line graphs the normal glucose metabolism in dogs used for testing this invention; the third graph illustrates the glucose utilization or production in the same number of dogs as sampled in the peripheral vascular and hepatic veins; and the bottom graph illustrates the plasma insulin in the normal group of dogs.
Figure 2:
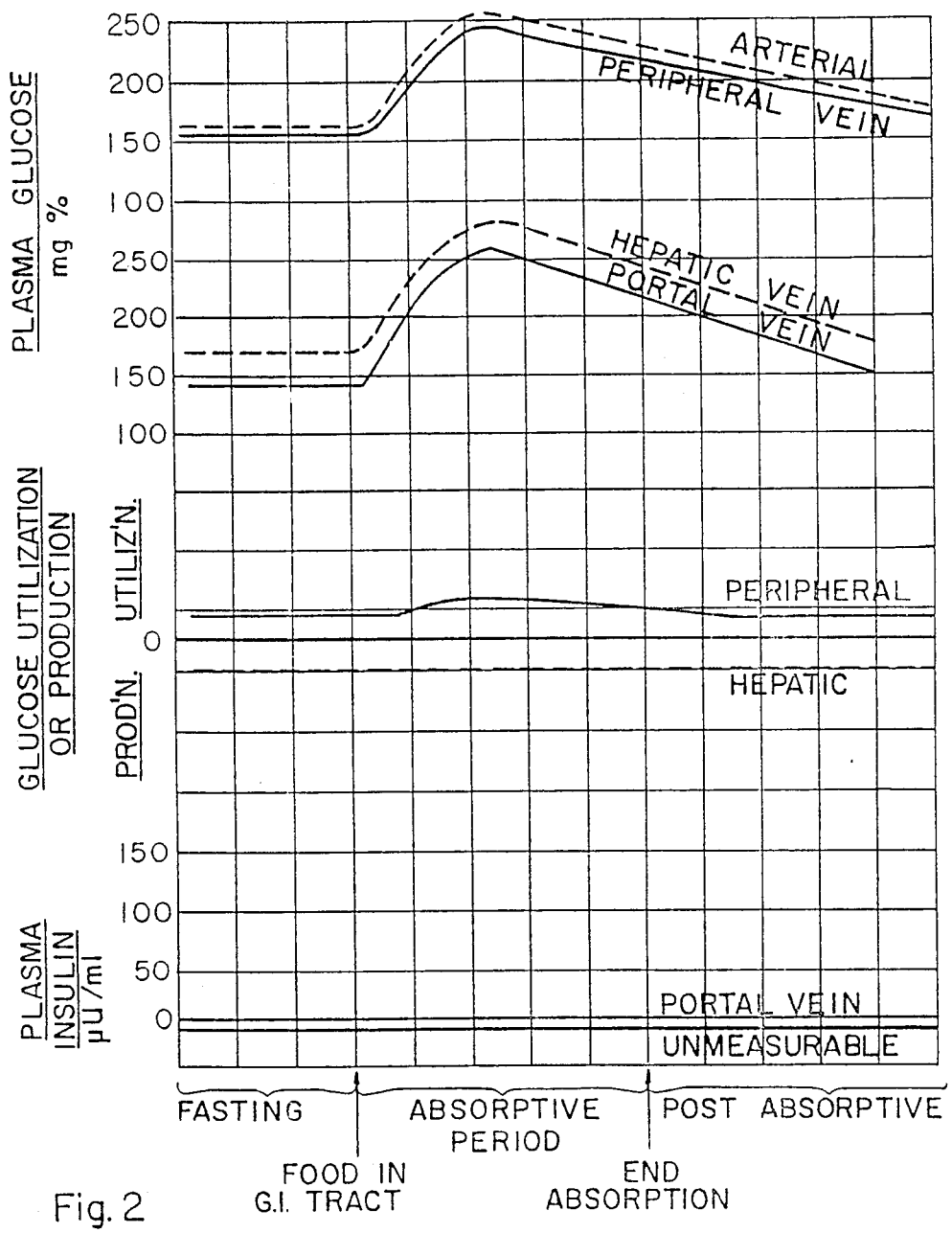
FIG. 2 is a multiple test graph of the dogs tested in FIG. 1 illustrating the effects caused by rendering the dogs completely diabetic as explained in the text hereof.
Figure 3:
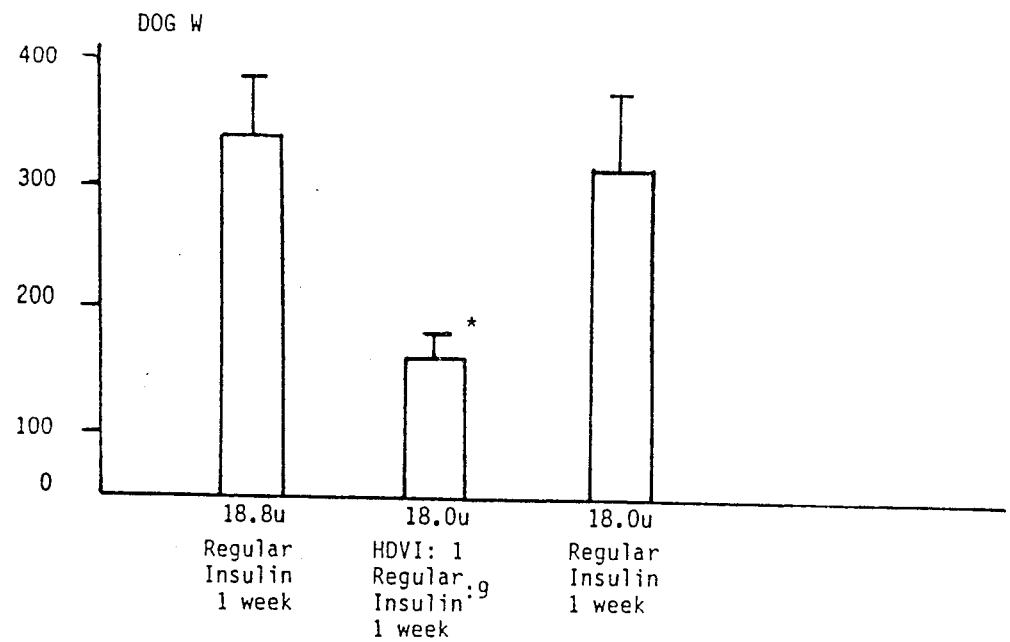
FIGS. 3-5 are graphs of three dogs, namely dog W, dog B and dog R after having been rendered diabetic, treated with regular insulin at the end of one week, the combined forms of this invention at the end of another week, and returned to regular insulin at the end of the third week.
Figure 4:
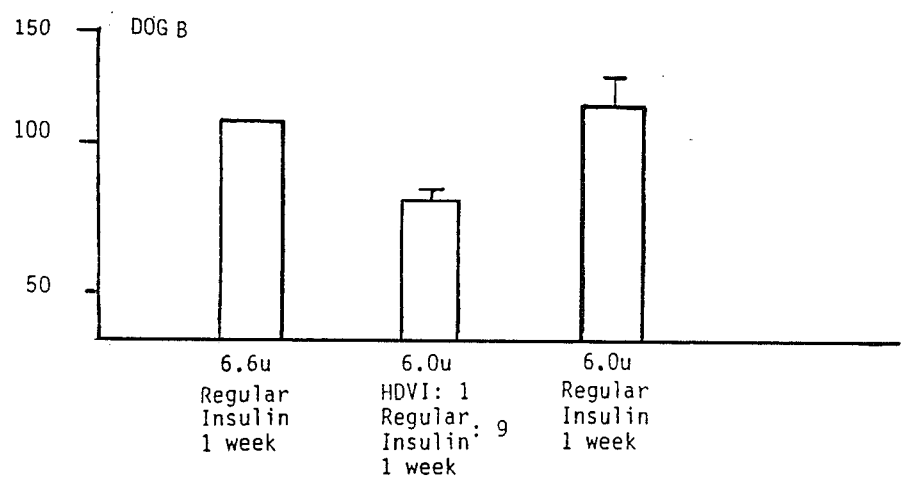
Figure 5:
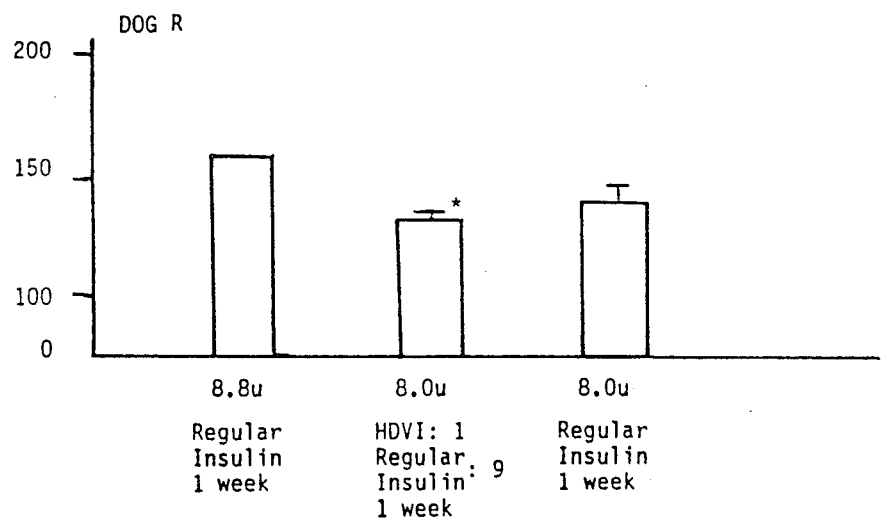

There are two separate and distinct components of the present invention:

First, free insulin as known and used since approximately the year of 1922 which heretofore has been employed by subcutaneous injection alone for the approximate control of hyperglycemia; and Secondly, a targeted insulin delivery system which has specificity for the hepatocytes, which are the specialized metabolic cells of the liver. Hereinafter, this will be referred to as a hepatocyte directed vesicle, or abbreviated as HDVI. This preferred directed delivery system utilizes a bipolar lipid for the majority of its vesicle membrane structure.

The targeting material described in U.S. Pat. No. b 4,377,567 and U.S. Pat. No. 4,603,044, which is only a minor constituent of the targeted vesicle system, has a specificity for the hepatocyte of the liver. The hepatocyte directed vesicle is then attracted to the receptor, and the vesicle releases its pharmacological cargo at this site. The two prior patents by co-inventor Geho, are both useful, but the hepatobiliary directed system of U.S. Pat. No. 4,603,044 is preferred.

Any chemical molecule capable of circulating in the bloodstream of a warm-blooded animal and attracted to the hepatobiliary receptors of the liver will serve as a target substance for this invention.

INTRODUCTION

Glucose in the blood is a primary energy nutrient for the body. Its level in the blood is carefully controlled so that it neither goes too high nor too low. Maintaining the blood level of glucose within narrow limits is so important that the body has, within the limits of current understanding of physiology, surprisingly sophisticated hormonal systems to prevent both hyperglycemia (blood glucose too high) and hypoglycemia (blood glucose too low).

The body has diseases that are characterized by blood glucose levels that are either too high (i.e. Diabetes Mellitus) or too low (i.e. hypoglycemia). This disclosure describes improved therapeutic means to correct abnormally elevated glucose levels that are found in Diabetes Mellitus. This invention recognizes the etiologies of these diseases of glucose metabolism. In order to understand the use of these new therapeutic inventions it is necessary to describe the normal physiological control mechanisms of the body. Once they are understood, the etiology of Diabetes can be recognized.

THE NORMAL PHYSIOLOGICAL CONTROL OF BLOOD GLUCOSE

Glucose is the main energy substance of the body and the blood is the means for transporting it to the various parts of the body. The blood glucose may be elevated by increasing its supply or blocking its removal. Conversely, blood glucose may be decreased by blocking its supply or enhancing its rate of removal from the blood. There are two sources of blood glucose: Digested food and glucose synthesized by the liver. Foods contain glucose, usually ingested in the form of starch or disaccharides and is converted to glucose by enzymes. The liver can also synthesize glucose from other food nutrients, such as simple sugar or amino acids which are derived from protein digestion. Therefore, the blood level of glucose is a summation of the functions of its rates of entry into the blood and its rate of removal.

PHARMACEUTICAL TREATMENT OF IMPAIRMENTS OF GLUCOSE METABOLISM (A) Diabetes Mellitus (Insulin Deficient)
  (a) Etiology: Diabetes Mellitus is caused by a deficiency of insulin.
  (b) Therapeutic Goal: The goal of therapy is to replace the deficient hormone (insulin) in such a manner that normal physiology is restored.
  (c) Achieving the Goal: It has been discovered, according to this invention, that in contrast to current medical thought two simultaneous modes of insulin replacement are necessary: (1) insulin to the liver and (2) insulin to the peripheral tissues. In order to provide insulin to both parts of the body new and improved forms of insulin are required since the currently administered insulin (by injection) serves only the peripheral tissues.
  (d) Means to Deliver Insulin to the Liver: Insulin, delivered by using the HDV-Insulin system (Hepatocyte Deliver Vesicle containing Insulin), administered orally, by pump or parenterally meets this requirements. Dosages range from 0.001 to 100.0 units/day depending on the patient and the specific HDVI preparation.
  (e) Means to Deliver Insulin to Peripheral Tissues: Peripheral tissues are supplied by parenteral forms of regular or delayed release forms of insulin.

(f) Preferred Means for Treating DIABETES with combined HDVI and Insulin: It is a discovery of this invention that free insulin and HDVI combined Insulin will produce the most natural reaction of any known prior theory, and at dosage levels of suprisingly low total units.

(i) Pump Therapy

Using a continuous infusion pump (such insulin pumps are now marketed), a mixture of HDVI and free Insulin are constantly administered subcutaneously or intravenously. This combination is effective and safe because the free insulin treats the peripheral tissues with a constant low dose of insulin, enabling the muscle and fat tissues to take in glucose to meet their energy requirements. At the same time, the liver receives the HDVI. During the fasting periods, the HDVI only suppresses the hepatic production of glucose, which is desirable.

During meals, the HDVI will activate the liver to store the ingested glucose as glycogen. When gastrointestinal absorption of glucose stops, the HDVI reverts to its function of controlling the hepatic glucose release.

The HDVI (1) enables the liver to store ingested glucose and (2) reduces the amount of glucose synthesized denovo. Therefore, the outstanding benefit of this invention is that the amount of glucose that is required to be metabolized by the peripheral tissue is reduced, and the peripheral insulin requirement is reduced. This reduced free insulin requirement also lessens the possibility of hypoglycemic reactions. No form of current therapy can do this.

(ii) Injection Therapy

HDVI and Insulin (short-acting, intermediate and long-acting) are combined into one for injection. While single injections will work, several a day are better. Both forms of Insulin (HDVI and free insulin) are absorbed from the injection sites into the blood and they act in the same way as described under Pump Therapy.

(iii) Combination Oral HDVI and Parenteral Insulin

Some physicians and patients may prefer to inject the free forms of insulin (short-acting, intermediate or long-acting) to provide the peripheral tissues with insulin while taking the oral form of HDVI. Oral HDVI is taken 30-60 minutes prior to eating.

(iv) Combination of Oral HDVI or Parenteral HDVI with Oral Hypoglycemic Drug

Some physicians may prefer to treat their Type I patients, providing there is some residual insulin remaining in their beta cells to be released, with oral or parenteral HDVI to treat the liver while using oral hypoglycemic drugs, such as tolbutamide, acetohexamide, tolazamide or chlorpropamide, to release insulin for peripheral tissues. The HDVI would be given 30-60 minutes prior to meals, along with appropriate insulin releaser.

HEPATOCYTE DIRECTED VESICLE INSULIN (HDVI) TREATMENT OF INSULIN DEFICIENT DOGS

I. Purpose: To test the efficacy of HDVI in insulin deficient dogs.

II. Research plan:
 A. Induce insulin deficiency with intravenous doses of streptozotocin and alloxan.
 B. Establish levels of regular insulin required for moderate control of plasma glucose (between 100 and 200 mg%).
 C. Test the efficacy of a combination of regular insulin and HDVI (ratio 9:1), maintaining the total insulin dosage as in "B" above.

III. Methods:

Healthy mongrel dogs weighing 10-20 kg were selected for the study. Insulin deficiency was induced with separate, but simultaneous, intravenous doses of streptozotocin (40 mg/kg) and alloxan (40 mg/kg) after a twenty-four hour fast. Glucose (as 5% glucose in water) was administered subcutaneously to counter the hypoglycemia that occurs in the induction process. Plasma glucose was measured with a Beckman Glucose Analyzer. The dogs were fed once a day with a standard dog chow.

IV. Results:

Fasting blood was sampled on Monday, Wednesday and Friday of each week. Once a state of hyperglycemia was induced, moderate control of the hyperglycemia was achieved with regular insulin given twice daily. All three dogs had fasting glucose levels in the normal range at the beginning of the study. Forty-eight hours after inducing insulin deficiency, all dogs were hypoglycemic. The insulin dosages were individualized for each dog. Dog W required the highest insulin dosages. Dog W's glucose levels remained above 300 mg% even with the 18 units of regular insulin per day (given in divided doses at 9 A.M. and 5 P.M.). Dogs B and R had lower glucose levels with lower doses of insulin.

Once plasma glucose values were stable for about one week, the insulin regimen was changed so that the total insulin dosage was the same, but the composition was 90% regular insulin and 10% was HDVI. In all three dogs, the plasma glucose values decreased significantly. After a week's therapy on the combined regular insulin plus HDVI, the treatment was returned to the original regular insulin regimen. In all three dogs, the glucose values increased, and significantly so in Dogs W and B.

V. Discussion:

HDVI is a dose-form of insulin that is specific for hepatocytes. In this preliminary study, Dogs W, R, and B, which had a chemically-induced insulin deficiency, responded to a combination of free regular insulin and HDVI with lower plasma glucose levels than they had on regular insulin alone, with total dosage unchanged. The treatment period of combined Regular Insulin and HDVI was followed by a treatment period of Regular Insulin alone.

Refer to the FIGS. 1-5 of the drawings for a graphic illustration of the foregoing discussion. The various stages in this study, as set forth above, will be self-explanatory, or may be observed in conjunction with the description of the drawings, supra.

The combine HDVI-Regular insulin treatment is more efficacious than Regular insulin alone because it supplies the insulin to both the hepatocytes and the peripheral tissues.

After having studied the test results of this invention on dogs, a further study was initiated to use mature Charles River rats, an animal that is employed regularly for studies of this kind.

Objective: To test the hypothesis that a combined dose of Hepatocyte Directed Vesicle Insulin (HDVI) and Regular Insulin (RI) is more effective in reducing plasma glucose in diabetic rats than either form of insulin alone.

Research Plan: Mature female Charles River rats (250 g) are given 5 mg streptozotocin intraperitoneally after a 24-hour fast to induce insulin deficiency. One week later the rats are randomly assigned into four groups: control, FI, HDVI, and HDVI+FI, without prescreening of animals for glucose levels. Blood is obtained by tail vein bleeding. Glucose is determined by a Beckman Glucose Analyzer.

Prior to dosing, a baseline tail vein glucose level is obtained. The dosages are a total of 1.0 units of insulin per rat (approximately 4.0 units/kg body weight). The solutions are adjusted so that each rat receives 0.2 ml subcutaneously. The HDVI-FI combination is 0.5 units HDVI and 0.5 units FI, given separately, so that the total dosage is 1 unit/rat. Blood is obtained as for the baseline at 3.5 hours post-dosing. Food and water are permitted throughout. The regular insulin is Lilly 0500 porcine insulin, diluted on the day of study.

Figure 6:
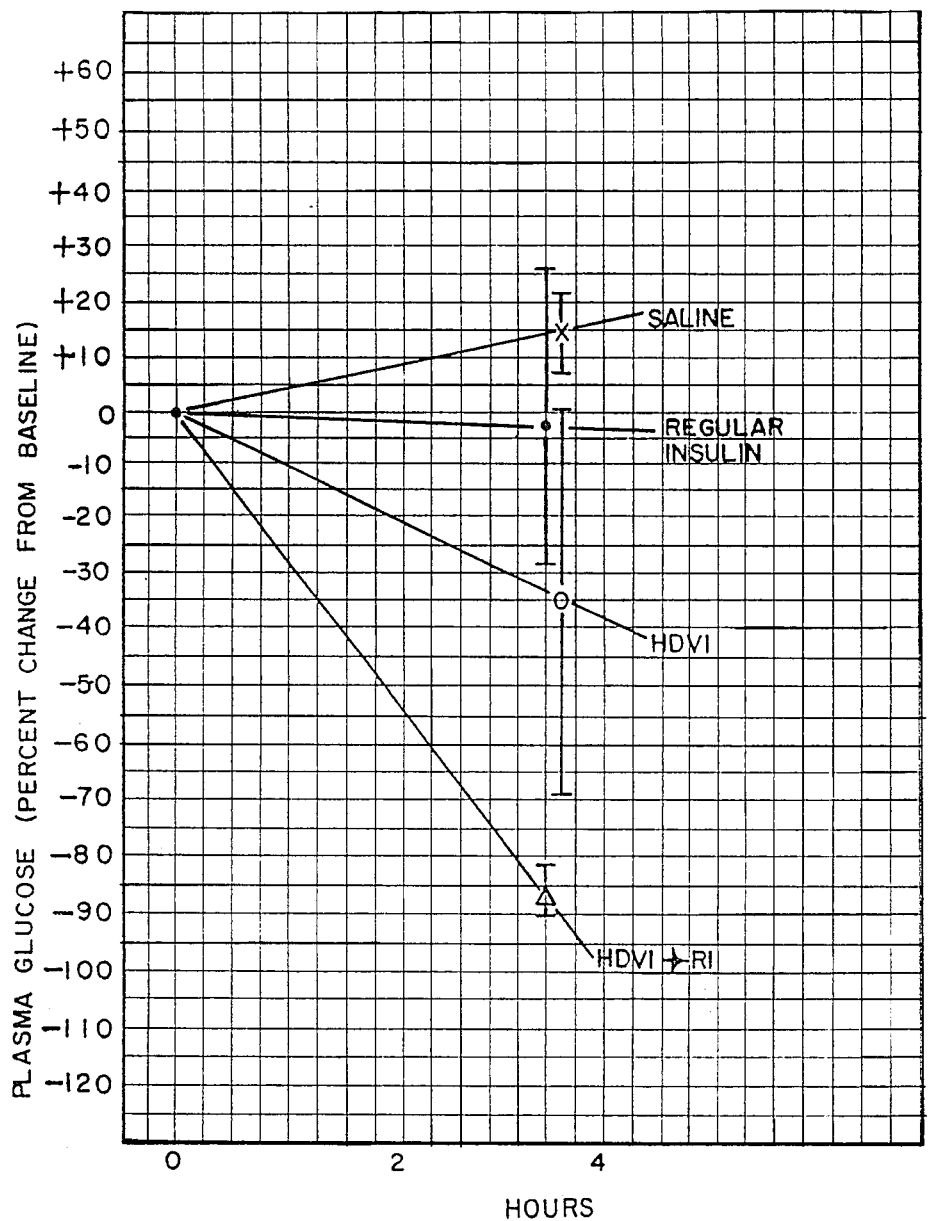
FIG. 6 is a graph summarizing the data listed in the tables set forth hereinafter.

Results: The results are set forth in the graph of FIG. 6. Control rats tended to increase their glucose levels (+14% +/− 8), but the variation was high enough that the rise was not statistically significant. See the line labeled "Saline" in FIG. 6. Free insulin alone brought only a −2% effect, and the HDVI reduced the glucose level below base line by a good and useful amount of −34%.

However, the combined effect was large (−86%) with an extremely small standard deviation (+/− 4%). This result is highly significant compared to all other groups and can clearly be seen as a synergistic effect.

Discussion: Regular Insulin and HDVI at dosages of 1 unit/rat (average weight 200-250 g) have useful hypoglycemic effects. The similarity of effects is not unlike those demonstrated in the dog study supra. The combined HDVI-FI effect, however, is of considerable magnitude, dropping the glucose levels to the lowest levels of what could be considered normal. The percent decrease of plasma glucose was −86% +/− 4%. The narrowness of the standard deviation of the mean is striking. Certainly the degree of the hypoglycemic effect is unexpected with the combined HDVI-FI dosage when it is compared to the individual responses of the HDVI and FI. The effects are not additive (−42 for HDVI and −16 for RI equal −58%, whereas the HDVI-FI effect is −86%).

The mechanism of this combined effect is not known. It could be due to a combined reduction of hepatic glucose production that results in a lowered peripheral glucose load, which requires less regular insulin to lower peripheral glucose levels.

Conclusion: The two separate studies conducted on separate test models, has proven the the combined HDVI-FI is more efficacious as a hypoglycemic treatment for insulin deficiency than equal total doses of HDVI or regular free insulin alone.

What is claimed is:

1. A method of stimulating normal glucose metabolism in a warm blooded animal wherein said animal has excess blood glucose due to insulin deficiency comprising: simultaneously administering an effective amount of insulin encapsulated liposome wherein said liposome has a target moiety recognizable by the hepatocyte receptors of the liver and free insulin in an amount sufficient for peripheral needs.

2. The method of claim 1, wherein the free insulin is a predominant portion of the total.

3. A method of stimulating normal glucose metabolism in a warm blooded animal wherein said animal has excess blood glucose levels and insufficient liver function by reason of insulin deficiency from pancreatic source comprising:
simultaneously administering an effective dose of insulin as determined by conventional diagnostic means wherein about one percent of the insulin is encapsulated with a lipid membrane liposome, which liposome has a target moiety recognizable by the hepatocyte receptors of the liver.

* * * * *